(12) United States Patent
Zhu et al.

(10) Patent No.: US 9,347,902 B2
(45) Date of Patent: May 24, 2016

(54) TESTER FOR MEASURING INSULATING PROPERTIES OF CROSS-LINKED POLYETHYLENE

(71) Applicants: Tianjin Electric Power Corporation, Tianjin (CN); State Grid Corporation of China, Beijing (CN)

(72) Inventors: Xiaohui Zhu, Tianjin (CN); Zhengzheng Meng, Tianjin (CN); Fengzheng Zhou, Tianjin (CN)

(73) Assignees: Tianjin Electric Power Corporation, Tianjin (CN); State Grid Corporation of China, Beijing (CN)

( * ) Notice: Subject to any disclaimer, the term of this patent is extended or adjusted under 35 U.S.C. 154(b) by 443 days.

(21) Appl. No.: 14/071,681

(22) Filed: Nov. 5, 2013

(65) Prior Publication Data

US 2014/0055149 A1    Feb. 27, 2014

Related U.S. Application Data

(63) Continuation-in-part of application No. PCT/CN2012/080253, filed on Aug. 16, 2012.

(30) Foreign Application Priority Data

Dec. 13, 2011    (CN) .......................... 2011 1 0415671

(51) Int. Cl.
| | |
|---|---|
| *G01R 27/08* | (2006.01) |
| *G01N 27/04* | (2006.01) |
| *G01R 27/26* | (2006.01) |
| *G01N 27/20* | (2006.01) |
| *G01R 31/12* | (2006.01) |

(52) U.S. Cl.
CPC .............. *G01N 27/04* (2013.01); *G01N 27/205* (2013.01); *G01R 27/2623* (2013.01); *G01R 31/1263* (2013.01)

(58) Field of Classification Search
CPC ............. G01R 27/206; G01R 27/2623; G01R 31/1263; G01N 27/04; G01N 27/08; G01N 27/205; G06F 23/284; G06F 23/2962
See application file for complete search history.

(56) References Cited

U.S. PATENT DOCUMENTS 3,753,098 A * 8/1973 Sambhu ............. G01R 27/2635
324/441

\* cited by examiner

*Primary Examiner* — Minh N Tang
(74) *Attorney, Agent, or Firm* — Matthias Scholl, PC; Matthias Scholl

(57) ABSTRACT

A tester for measuring insulating properties of cross-linked polyethylene, the tester including: a housing including a control panel; a high voltage chamber including an insulating cover, a fixed frame, an insulating oil cup, a high voltage electrode, a ground electrode, and a temperature control device; and a test circuit including a high voltage power supply, a voltmeter, a timer, an overcurrent protection device, and a digital thermometer. The high voltage chamber and the test circuit are arranged inside the housing. The control panel is arranged on the housing. The insulating cover is disposed on the high voltage chamber. The fixed frame is disposed inside the high voltage chamber. The insulating oil cup is mounted on the fixed frame. The high voltage electrode and the ground electrode are disposed oppositely inside the insulating oil cup. The temperature control device is disposed beneath the insulating oil cup.

2 Claims, 6 Drawing Sheets

TESTER FOR MEASURING INSULATING PROPERTIES OF CROSS-LINKED POLYETHYLENE

CROSS-REFERENCE TO RELATED APPLICATIONS

This application is a continuation-in-part of International Patent Application No. PCT/CN2012/080253 with an international filing date of Aug. 16, 2012, designating the United States, now pending, and further claims priority benefits to Chinese Patent Application No. 201110415671.0 filed Dec. 13, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

The invention relates to the field of power cables, and more particularly to a multifunctional tester for measuring the insulating properties of cross-linked polyethylene (XLPE).

2. Description of the Related Art

The physical and chemical performances of cross-linked polyethylene (XLPE) are subject to its crosslinking degrees and operating environments, so that it is necessary to know the electric performance differences of XLPE. At room temperature or a slightly lower temperature, the physical and chemical performance differences of XLPE having different crosslinking degrees may be small, but as a polymer material in a semi-crystalline state, the XLPE has a relatively low melting temperature. In conditions of a relatively high temperature, the physical and chemical performances of XLPE having different crosslinking degrees obviously vary from each other because of the semi-crystalline property of the XLPE. In actual operation of power cable, an operating temperature of the insulating layer may reach between 70 and 90° C., and the operating temperature may reach 105° C. in emergency. Thus, the electric performance of XLPE is required to be tested at different environment temperatures.

Testers for measuring insulating properties of XLPE often employ a needle-plate electrode structure. One electrode of a high voltage terminal employs a needle-like structure having a certain radius of curvature, and the other electrode of a low voltage terminal employs a circular plate structure. Meanwhile, a handheld infrared thermometer is used to measure the temperature of the insulating oil. However, testers of such structures have the following problems:

1. As the needle-plate electrode structure is used, when a test piece is mounted, uneven force may be exerted on the test piece because of manual operation, thereby influencing the strength of the voltage field.

2. The needle-like electrode is easy to be damaged during the test, thereby resulting in variation of the radius of curvature.

3. It is difficult to operate and real-time monitor the variation of the oil temperature when using the handheld infrared thermometer to measure the temperature of the insulating oil. In a word, measuring conditions of the existing tester easily change, which results in inaccurate measuring.

SUMMARY OF THE INVENTION

In view of the above-described problems, it is one objective of the invention to provide a tester for measuring insulating properties of cross-linked polyethylene (XLPE). The tester is reasonably designed and test results therefrom are capable of accurately reflecting the real insulating properties of XLPE.

To achieve the above objective, in accordance with one embodiment of the invention, there is provided a tester for measuring insulating properties of cross-linked polyethylene comprising: a housing, the housing comprising a control panel; a high voltage chamber, the high voltage chamber comprising an insulating cover, a fixed frame, an insulating oil cup, a high voltage electrode, a ground electrode, and a temperature control device; and a test circuit, the test circuit comprising a high voltage power supply, a voltmeter, a timer, an overcurrent protection device, and a digital thermometer. The high voltage chamber and the test circuit are arranged inside the housing. The control panel is arranged on the housing. The insulating cover is disposed on the high voltage chamber; the fixed frame is disposed inside the high voltage chamber; the insulating oil cup is mounted on the fixed frame; the high voltage electrode and the ground electrode are disposed oppositely inside the insulating oil cup; the temperature control device is disposed beneath the insulating oil cup for controlling an oil temperature. Two ends of the insulating oil cup are connected to the high voltage electrode and the ground electrode, respectively. One end of the high voltage power supply is connected to the overcurrent protection device; an input end of the high voltage power supply is connected to the voltmeter, and the voltmeter is connected to the timer. The digital thermometer is connected to the temperature control device to test the oil temperature in the insulating oil cup. Besides, during the test, in order to uniformly heat the oil in the insulating oil cup, a stirrer is arranged inside the insulating oil cup.

In a class of this embodiment, the high voltage electrode is a cylindrical electrode comprising an upper part comprising a cylindrical copper electrode and a lower part comprising a copper cylinder. The ground electrode is a circular copper electrode.

Advantages of the invention are summarized as follows:

The tester of the invention is employed to test the test sample of XLPE by regulating the voltage between the high voltage electrode and the ground electrode and the oil temperature inside the insulting oil cup. The voltage regulation and the display thereof, the temperature regulation and the display thereof, the timing set and the display thereof, and the overcurrent protection are realized, the environment stability for testing the insulating properties of the XLPE is ensured, so that the insulating properties of the XLPE in different operating temperatures and different compressive strength is really and effectively measured. Meanwhile, the electrodes employ the line-plate electrode structure to overcome errors existing in the traditional needle-plate electrode structure resulting from the uniform force, uncertainty of the contact area between the electrodes and the test sample, or damages occurring in the electrodes, and to eliminate errors resulting from different testing conditions, so that the insulating properties of the XLPE test sample is accurately reflected.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a tester for measuring insulating properties of cross-linked polyethylene are described below. It should be noted that the following examples are intended to describe and not to limit the invention.

Figure 1:
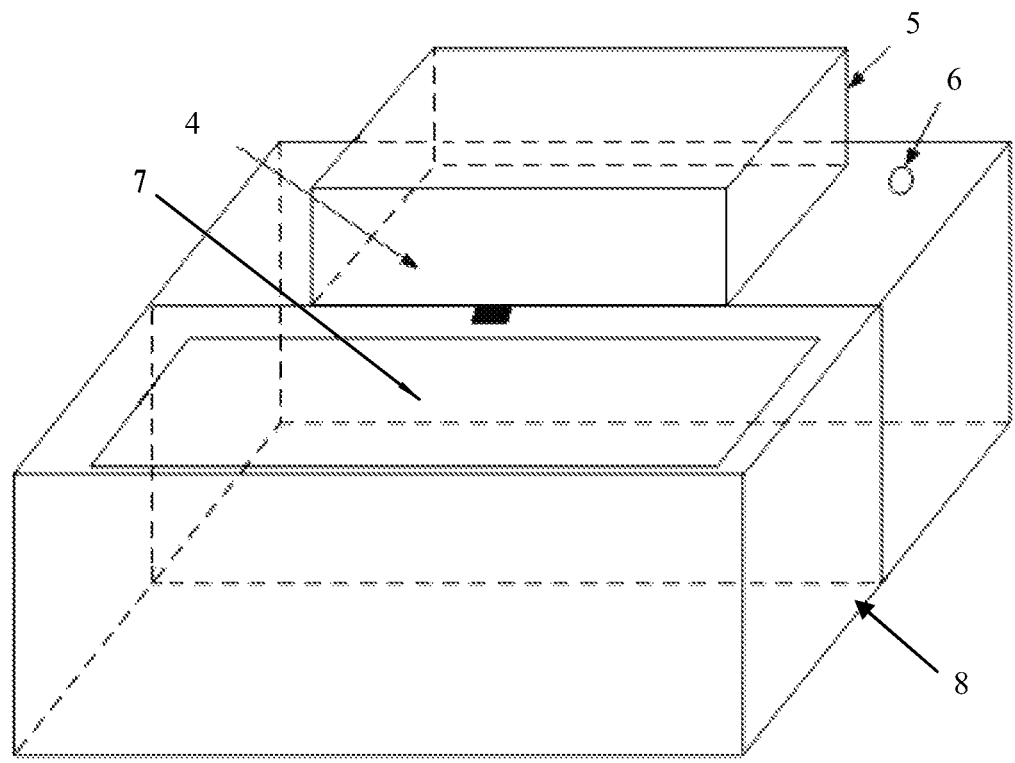
FIG. 1 is a stereogram of a tester for measuring insulating properties of cross-linked polyethylene in accordance with one embodiment of the invention.

As shown in FIG. 1, a tester for measuring insulating properties of cross-linked polyethylene comprises: a housing 8, the housing 8 comprising a ground terminal 6 and a control panel 7; a high voltage chamber 4, the high voltage chamber 4 comprising an insulating cover 5, a fixed frame 14, an insulating oil cup 15, a high voltage electrode 11, a ground electrode 12, and a temperature control device 16; and a test circuit, the test circuit comprising a high voltage power supply, a voltmeter, a timer, an overcurrent protection device, and a digital thermometer. The high voltage chamber 4 and the test circuit are arranged inside the housing 8. The control panel 7 is arranged on the housing 8. The insulating cover 5 is disposed on the high voltage chamber 4.

Figure 2:
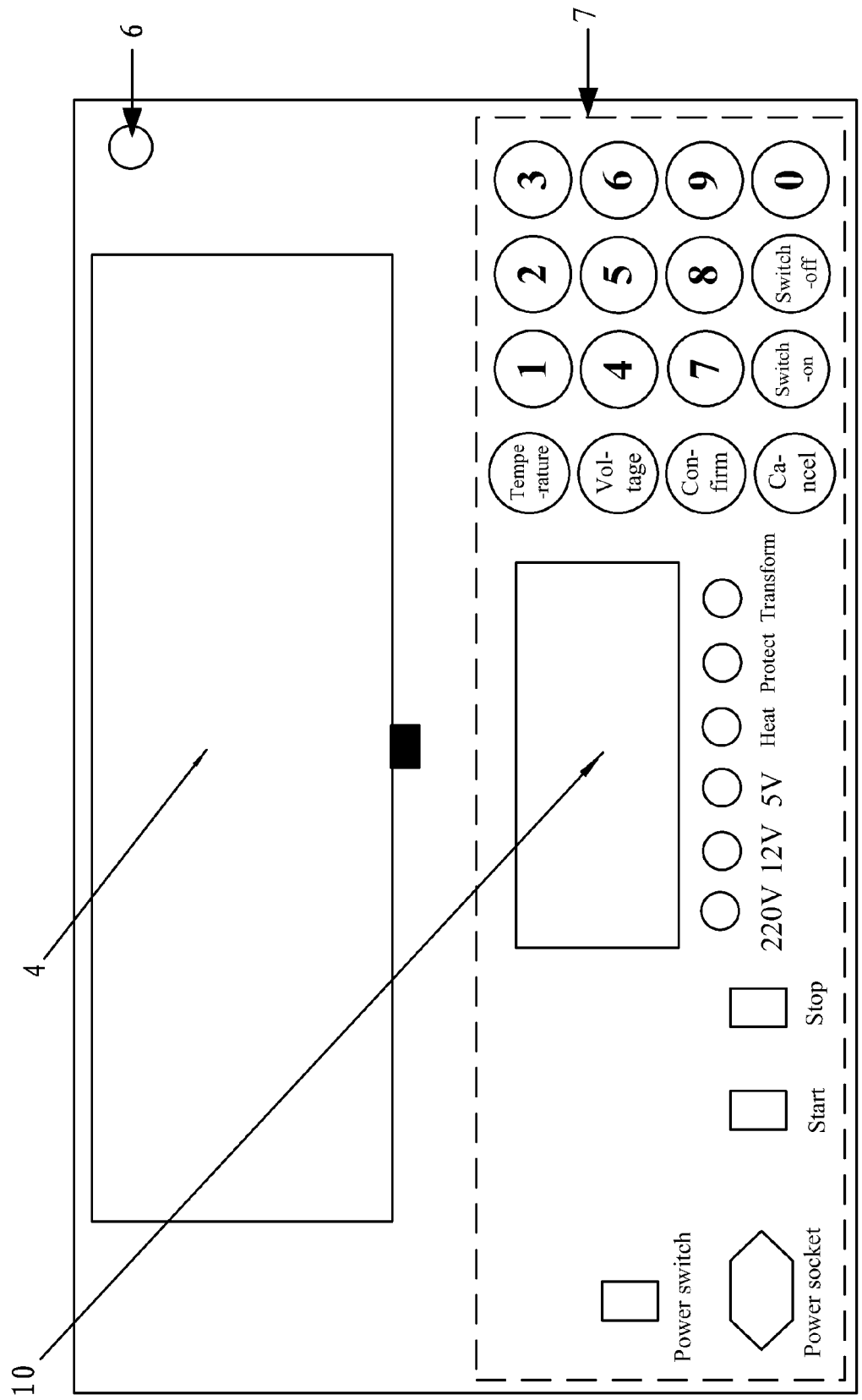
FIG. 2 is a top view of a tester for measuring insulating properties of cross-linked polyethylene in accordance with one embodiment of the invention.

As shown in FIG. 2, the control panel 7 comprises a power socket, a power switch, a start key, a stop key, an LCD screen 10, status indicators, a temperature regulation key, a voltage regulation key, and digital keys and is connected to the test circuit for realizing the voltage regulation and the display thereof, the temperature regulation and the display thereof, and the timing set and the display thereof.

Figure 3:
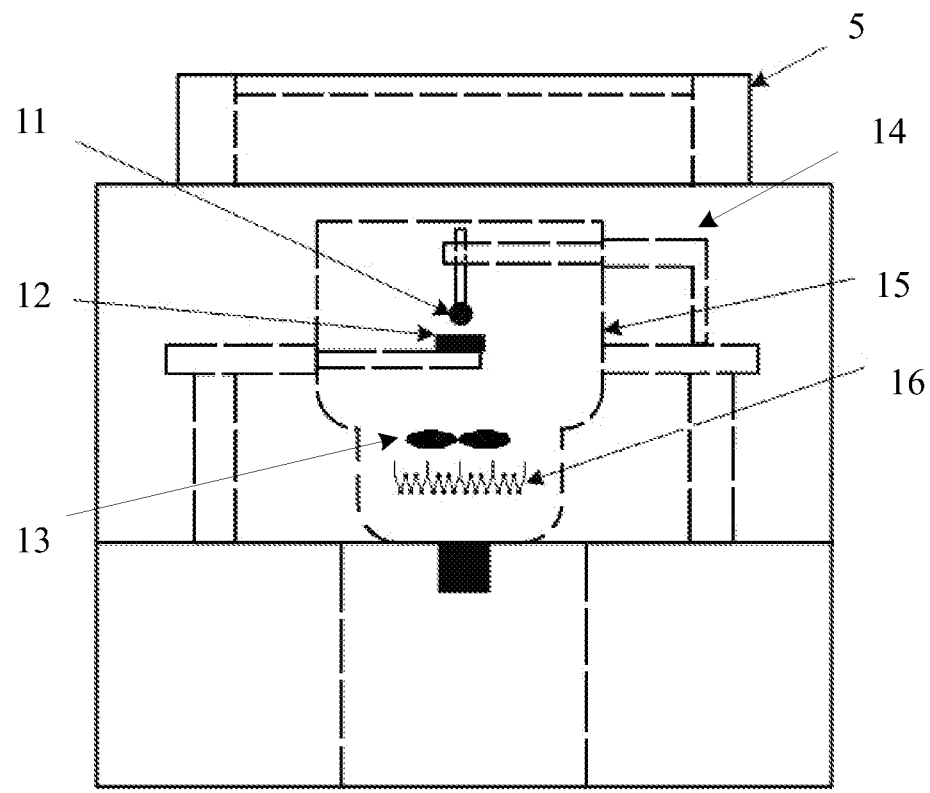
FIG. 3 is a structure diagram of an inner structure of a high voltage chamber of FIG. 2 in accordance with one embodiment of the invention.

As shown in FIG. 3, the fixed frame 14 is disposed inside the high voltage chamber 4; the insulating oil cup 15 is mounted on the fixed frame 14; and the high voltage electrode 11 and the ground electrode 12 are disposed oppositely inside the insulating oil cup 15. Two ends of the insulating oil cup 15 are connected to the high voltage electrode 11 and the ground electrode 12, respectively. The ground electrode 12 is connected to the ground terminal 6 arranged on the housing 8. The temperature control device 16 is disposed beneath the insulating oil cup 15 for controlling the oil temperature. The high voltage electrode 11 and the ground electrode 12 arranged inside the insulating oil cup 15 employ a structure of line-plate electrodes rather than a conventional structure of the needle-plate electrodes.

Figure 4A:
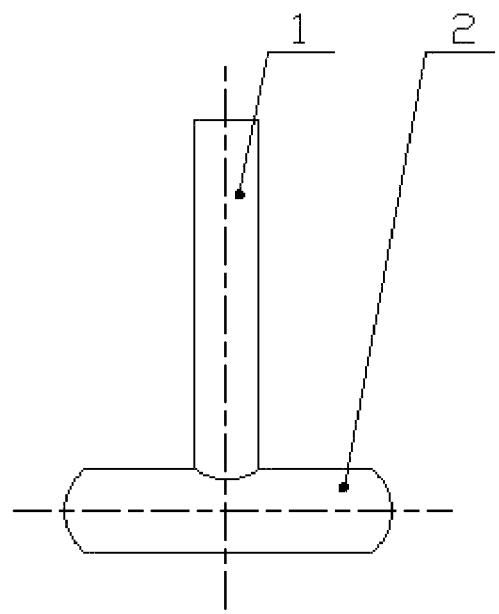
FIG. 4a is a structure diagram of a high voltage electrode in an insulating oil cup in FIG. 3.
Figure 4B:
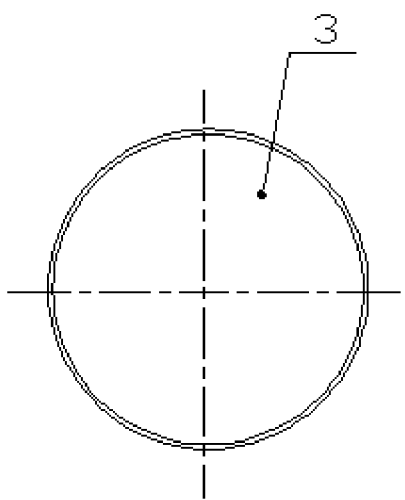
FIG. 4b is a structure diagram of a ground electrode in an insulating oil cup in FIG. 3.

As shown in FIG. 4a, the high voltage electrode 11 arranged in an upper part of the insulating oil cup is a cylindrical electrode. A lower part of the cylindrical electrode is a copper cylinder 2 having a length of 10 mm and a diameter of 5 mm, and an upper part of the cylindrical electrode is a cylindrical copper electrode 1 having a length of 16 mm and a diameter of 3 mm. The ground electrode 12 arranged in a lower part of the insulating oil cup is a disc-shaped electrode 3 having a thickness of 2.5 mm and a diameter of 15 mm, the disc-shaped electrode is made of copper. An upper connecting surface and a lower connecting surface of the disc-shaped electrode are curved convex surfaces. Besides, in order to uniformly heat the oil in the insulating oil cup 15, a stirrer 13 is arranged inside the insulating oil cup 15.

Figure 5:
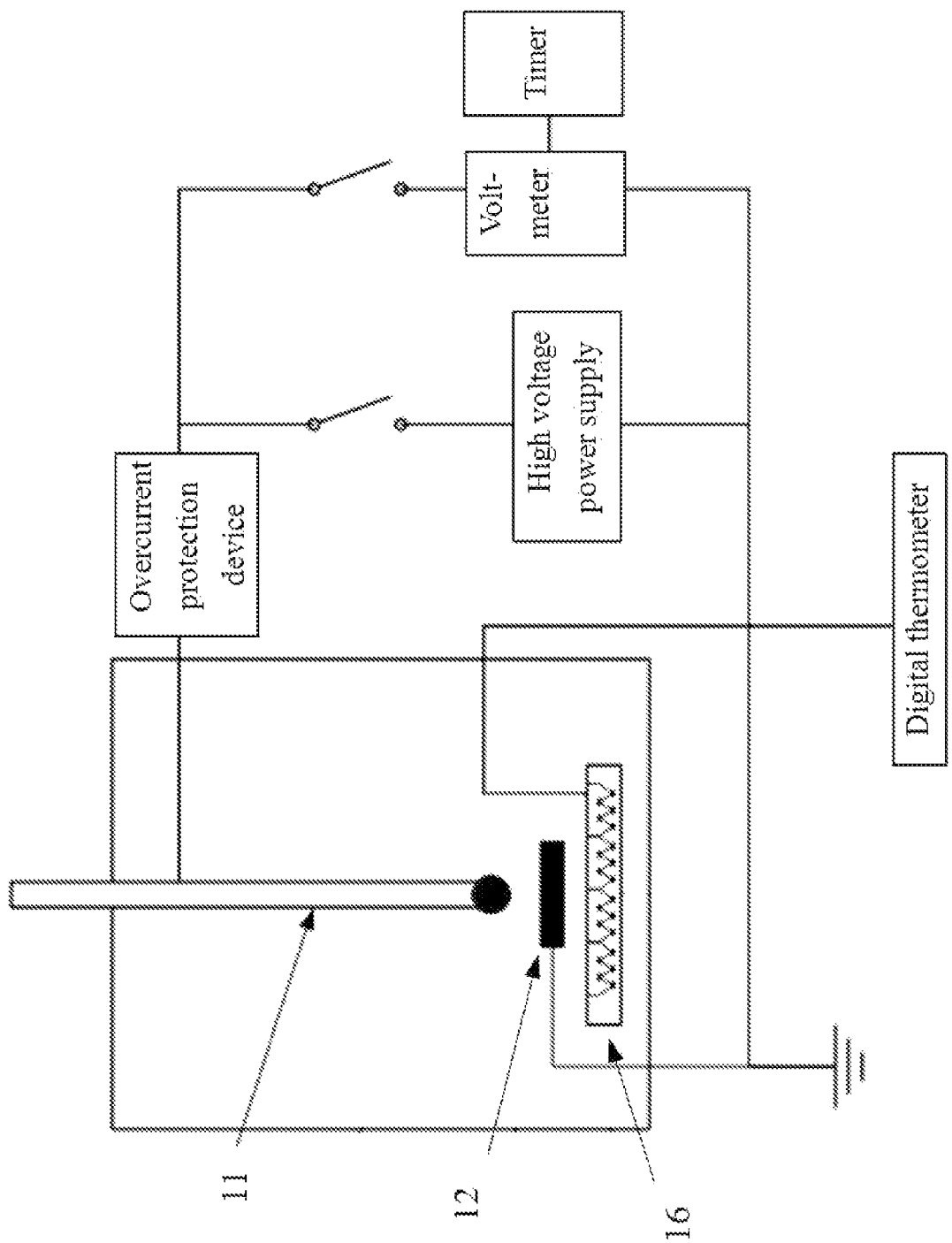
FIG. 5 is a circuit schematic diagram of a tester for measuring insulating properties of cross-linked polyethylene in accordance with one embodiment of the invention.

The test circuit is arranged inside the housing 8, as shown in FIG. 5. The test circuit comprises the high voltage power supply, the voltmeter, the timer, the overcurrent protection device, and the digital thermometer. Two ends of the insulating oil cup 15 are connected to the high voltage electrode 11 and the ground electrode 12, respectively. One end of the high voltage power supply is connected to the overcurrent protection device which is capable of instantly powering off when the test sample is punctured to protect the electrode. An input end of the high voltage power supply is connected to the voltmeter, and the voltmeter is connected to the timer for accurately displaying the applied voltage value, the breakdown voltage value, and the duration of the applied voltage. The digital thermometer is connected to the temperature control device 16 to test the oil temperature in the insulating oil cup 15. The operation keys arranged on the control panel 7 are used to gradually regulate the oil temperature in the insulating oil cup by the temperature control device 16. The test circuit and the control panel 7 are combined to realize the voltage regulation and the display thereof, the temperature regulation and the display thereof, the timing set and the display thereof, and the overcurrent protection. A maximum output voltage is 80 kV, a highest oil temperature is 110° C., and an accuracy of the timer is ±0.1 s, an accuracy of the digital voltmeter is ±0.5%, and an accuracy of the temperature control device is ±2° C.

A method for operating the tester for measuring the insulating properties of cross-linked polyethylene of the invention comprises the following steps:

1. placing an XLPE test sample between the high voltage electrode 11 and the ground electrode 12, and adjusting the positions of the two electrodes;

2. allowing an oil surface in the insulating oil cup 15 to be higher than the high voltage electrode 11;

3. connecting the power supply and the ground terminal, and inspecting the test circuit;

4. presetting a test voltage value and a test temperature value;

5. pressing the start key on the control panel 7 to start the test; and 6. recording the breakdown voltage value, the duration for the breakdown, and the real-time oil temperature if the test sample is punctured; or decreasing the voltage to zero at a certain rate if the breakdown does not occur and the voltage value reaches the preset test voltage value, and turning off the power.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A tester for measuring insulating properties of cross-linked polyethylene, the tester comprising:
   a) a housing (8), the housing (8) comprising a control panel (7);
   b) a high voltage chamber (4), the high voltage chamber (4) comprising an insulating cover (5), a fixed frame (14), an insulating oil cup (15), a high voltage electrode (11), a ground electrode (12), and a temperature control device (16); and
   c) a test circuit, the test circuit comprising a high voltage power supply, a voltmeter, a timer, an overcurrent protection device, and a digital thermometer;
   wherein the high voltage chamber (4) and the test circuit are arranged inside the housing (8);

the control panel (7) is arranged on the housing (8);

the insulating cover (5) is disposed on the high voltage chamber (4); the fixed frame (14) is disposed inside the high voltage chamber (4); the insulating oil cup (15) is mounted on the fixed frame (14); the high voltage electrode (11) and the ground electrode (12) are disposed oppositely inside the insulating oil cup (15); the temperature control device (16) is disposed beneath the insulating oil cup (15) for controlling an oil temperature;

two ends of the insulating oil cup (15) are connected to the high voltage electrode (11) and the ground electrode (12), respectively;

one end of the high voltage power supply is connected to the overcurrent protection device; an input end of the high voltage power supply is connected to the voltmeter, and the voltmeter is connected to the timer; and the digital thermometer is connected to the temperature control device (16) to test the oil temperature in the insulating oil cup (15).

2. The tester of claim 1, wherein the high voltage electrode (11) is a cylindrical electrode comprising an upper part comprising a cylindrical copper electrode (2) and a lower part comprising a copper cylinder (1); and the ground electrode (12) is a circular copper electrode.

\* \* \* \* \*